US011497427B2

(12) United States Patent
Govari et al.

(10) Patent No.: US 11,497,427 B2
(45) Date of Patent: *Nov. 15, 2022

(54) ADJUSTING ANNOTATION POINTS IN REAL TIME

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 210 days.

This patent is subject to a terminal disclaimer.

(21) Appl. No.: 16/817,532

(22) Filed: Mar. 12, 2020

(65) Prior Publication Data

US 2021/0282659 A1 Sep. 16, 2021

(51) Int. Cl.
*A61B 5/287* (2021.01)
*A61B 5/00* (2006.01)

(52) U.S. Cl.
CPC ............ *A61B 5/287* (2021.01); *A61B 5/7221* (2013.01)

(58) Field of Classification Search
CPC ....................................................... A61B 5/287
USPC ................................................. 600/508–509
See application file for complete search history.

(56) References Cited

U.S. PATENT DOCUMENTS

| 2015/0313511 | A1 | 11/2015 | Nabutovsky et al. |
| 2015/0317448 | A1 | 11/2015 | Razavi et al. |
| 2017/0042436 | A1 | 2/2017 | Harlev et al. |
| 2017/0086701 | A1* | 3/2017 | Stewart .................. A61B 5/287 |
| 2017/0311833 | A1 | 11/2017 | Afonso et al. |
| 2021/0133516 | A1* | 5/2021 | Govari ................. G06K 9/6284 |

* cited by examiner

*Primary Examiner* — Nicole F Lavert
(74) *Attorney, Agent, or Firm* — Frost Brown Todd LLC

(57) ABSTRACT

A system includes signal acquisition circuitry and a processing unit. The signal acquisition circuitry is configured to receive multiple intra-cardiac signals acquired by multiple electrodes of an intra-cardiac probe in a heart of a patient. The processing unit is configured to select a group of the intra-cardiac signals, extract a respective most-likely annotation value from each of the intra-cardiac signals in the group, in accordance with a likelihood criterion, identify in the group an intra-cardiac signal whose most-likely annotation value is statistically deviant in the group by more than a predefined measure of deviation, extract, from the intra-cardiac signal having the statistically deviant annotation value, at least a second-most-likely annotation value in accordance with the likelihood criterion, and, responsive to a statistical deviation of the second-most-likely annotation value, select a valid annotation value for the corresponding intra-cardiac signal.

15 Claims, 4 Drawing Sheets

ADJUSTING ANNOTATION POINTS IN REAL TIME

FIELD OF THE INVENTION

The present invention relates generally to intrabody medical procedures and instruments, and particularly to intrabody cardiac electrocardiogram (ECG) sensing and visualizing.

BACKGROUND OF THE INVENTION

When measuring and annotating internal-electrocardiogram (iECG) signals that are generated by a large number of electrodes, it may be desirable to process the signals (e.g., by a computer), in order to reduce the embedded noise.

Various methods exist for such iECG signal processing. For example, U.S. Pat. No. 9,314,179 describes an automatic method of determining local activation time (LAT) of four or more multi-channel cardiac electrogram signals which include a Ventricular channel, a mapping channel and a plurality of reference channels.

Another example is U.S. Pat. No. 10,441,187, which describes a system for diagnosing arrhytmias and directing catheter therapies by measuring, classifying, analyzing, and mapping spatial electrophysiological (EP) patterns within a body.

Yet another example is U.S. Pat. No. 9,888,862, which describes Systems and methods to automatically integrate measurements taken over multiple heart beats into a single cardiac map.

SUMMARY OF THE INVENTION

An embodiment of the present invention that is described herein provides a system including signal acquisition circuitry and a processing unit. The signal acquisition circuitry is configured to receive multiple intra-cardiac signals acquired by multiple electrodes of an intra-cardiac probe in a heart of a patient. The processing unit is configured to select a group of the intra-cardiac signals, extract a respective most-likely annotation value from each of the intra-cardiac signals in the group, in accordance with a likelihood criterion, identify in the group an intra-cardiac signal whose most-likely annotation value is statistically deviant in the group by more than a predefined measure of deviation, extract, from the intra-cardiac signal having the statistically deviant annotation value, at least a second-most-likely annotation value in accordance with the likelihood criterion, and, responsive to a statistical deviation of the second-most-likely annotation value, select a valid annotation value for the corresponding intra-cardiac signal.

In some embodiments, the processing unit is configured to define the measure of the deviation in terms of a standard score of the annotation values. In a disclosed embodiment, the processing unit is configured to calculate deviations of the annotation values over intra-cardiac signals acquired by a selected subset of spatially related electrodes located no more than a predefined distance from one another in the heart.

In an example embodiment, the processing unit is further configured to identify, for at least the statistically deviant most-likely annotation value, a group of alternative annotation values with decreasing likelihood ranks and to select the valid annotation value responsive to the statistical deviation and the likelihood ranks of the alternative annotation values. In another embodiment, the annotation values include Local Activation Times (LATs).

In some embodiments, the processing unit is configured to extract the most-likely annotation value in a given intra-cardiac signal by finding an extremum of the given intra-cardiac signal in a cardiac cycle, and to extract the second-most-likely annotation value by finding a second-highest local extremum of the intra-cardiac signal. In other embodiments, the processing unit is configured to extract the most-likely annotation value in a given intra-cardiac signal by finding an extremum derivative of the given intra-cardiac signal in a cardiac cycle, and to extract the second-most-likely annotation value by finding a second-highest local extremum of the derivative.

There is additionally provided, in accordance with an embodiment of the present invention, a method including receiving multiple intra-cardiac signals acquired by multiple electrodes of an intra-cardiac probe in a heart of a patient. A group of the intra-cardiac signals is selected. A respective most-likely annotation value is extracted from each of the intra-cardiac signals in the group, in accordance with a likelihood criterion. An intra-cardiac signal, whose most-likely annotation value is statistically deviant in the group by more than a predefined measure of deviation, is identified in the group. At least a second-most-likely annotation value is extracted from the intra-cardiac signal having the statistically deviant most-likely annotation value, in accordance with the likelihood criterion. Responsive to a statistical deviation of the second-most-likely annotation value, a valid annotation value is selected for the corresponding intra-cardiac signal.

There is further provided, in accordance with an embodiment of the present invention, a method to obtain a valid a local activation time of intra-cardiac electrocardiogram signals. The method includes acquiring a group of digitized signals representing intra-cardiac electrocardiogram (ECG) signals, and extracting a first best estimate of a valid local activation time from the group of ECG signals. Statistical characteristics are calculated for the group of ECG signals. A standard score is calculated for each signal in the group of ECG signals based on the group statistical characteristics. The standard score of each signal is compared with preset limits. The first best estimate of a valid local activation time is replaced with a local activation time of the signal having a standard score within the preset limits.

The present invention will be more fully understood from the following detailed description of the embodiments thereof, taken together with the drawings in which:

DETAILED DESCRIPTION OF EMBODIMENTS

Overview

Figure 1:
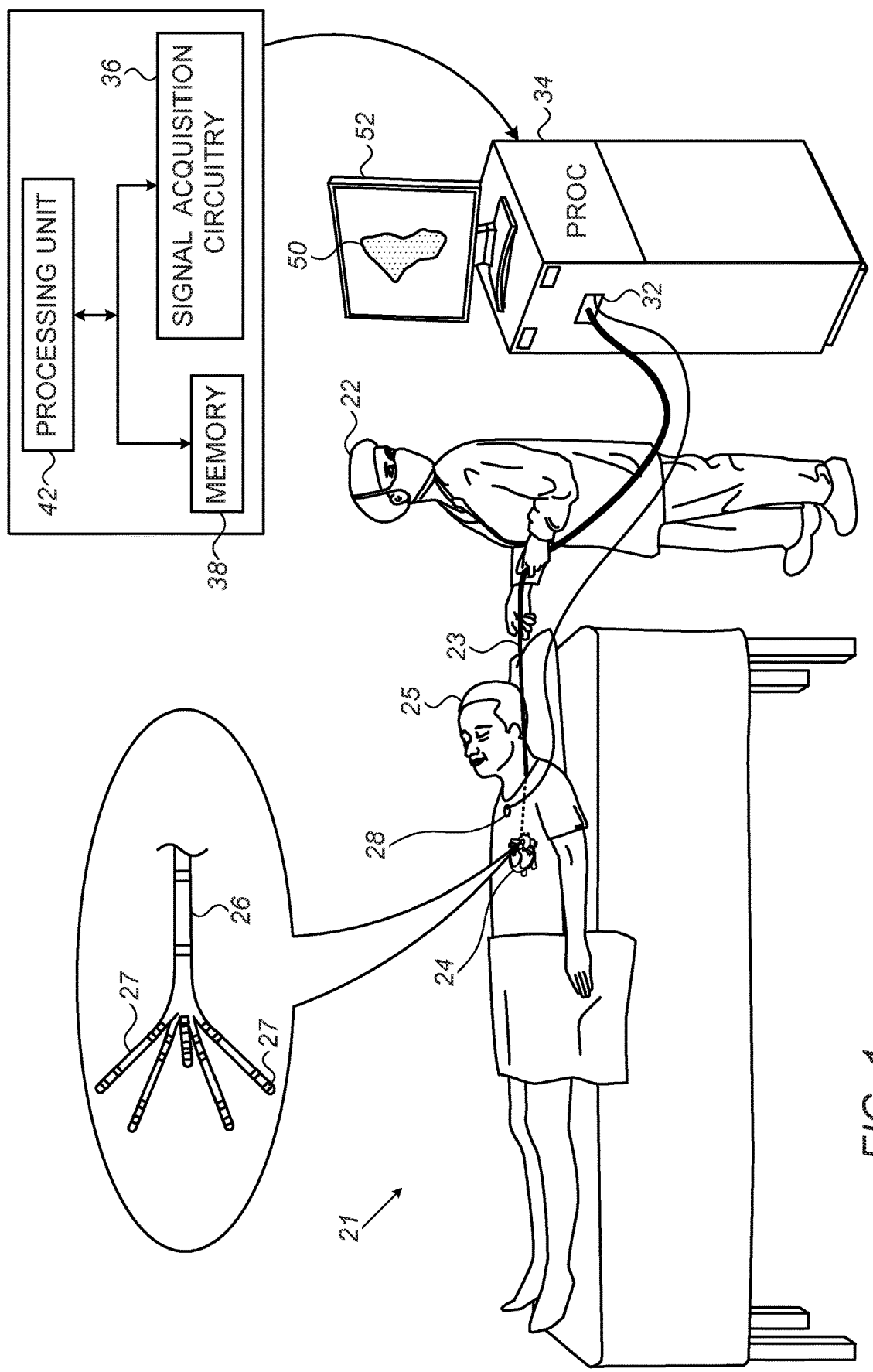
FIG. 1 is a schematic, pictorial illustration of an electro-anatomical system for multi-channel measurement of intra-cardiac ECG signals, in accordance with an embodiment of the present invention.

Intra-cardiac probe-based (e.g., catheter-based) cardiac diagnostic and therapeutic systems may measure multiple intra-cardiac signals, such as electrocardiograms (ECG), during an invasive procedure. Such systems may acquire the multiple intra-cardiac signals using electrodes (also referred to hereinafter as "distal electrodes") that are fitted at the distal end of the probe. The measured signals are typically analyzed, and Local Activation Time (LAT) values are annotated, which may be used to provide a physician with visual cardiac information such as 3-D mapping of the source of pathological electrical patterns within the heart of the patient, and to support corrective medical procedures such as ablation.

The measured signals are typically weak, with a low Signal to Noise Ratio (SNR). Moreover, pathological electrocardiograms such as those caused by atrial flutter or atrial fibrillation may exhibit multiple peaks in a cardiac cycle, which complicate the measurement of LAT values. On the other hand, many electrodes are used, and, hence, there may be some redundancy in the data that the system receives from the electrodes.

Embodiments of the present invention that are disclosed herein provide intra-cardiac probe-based electro-anatomical measurement and analysis systems and methods that use statistical characteristics of the signals that the distal electrodes collect, to improve the quality and reliability of the collected data. The methods are fast, and hence may be done in real-time; e.g., during the invasive procedure.

Although the description hereinbelow refers to annotation value of Local Activation Time (LAT), other suitable signal parameters may be used, mutatis mutandis, in various embodiments of the present invention. Accordingly, the term "annotation value" includes other parameters as well as those related to the LAT.

According to embodiments, the most likely LAT annotation value of a measured intra-cardiac signal may be estimated by analyzing the intracardiac signal using a preset criterion. Several LAT estimate criteria may be used, including (but not limited to) maximum signal voltage event, minimum signal voltage event, maximum rate of change of positive voltage slopes event, and the maximum rate of change of negative voltage slopes event. The LAT estimate is then set to the occurrence time of the event, according to the selected criterion. The value of the voltage or the slope at the event will be referred to herein as the "y value".

As mentioned above, due to noise and/or to heart pathologies, such LAT estimates may sometimes erroneously identify a local extremum (maximum or minimum, according to the criterion) rather than the desired extremum. In those cases, a more accurate LAT estimate may be achieved if the processor re-analyzes the signal, using the same criterion, but searching for the second, third, fourth or other extremum. (To avoid confusion between minimum/maximum/high/low, we will use hereinbelow terms such as "best LAT estimate," "second best, "third best," etc. For the maximum voltage or maximum dv/dt event, the best estimate is the highest voltage or highest dv/dt; the second best is the second highest local maximum, etc. Similarly, for the minimum voltage or the minimum dv/dt event, the best estimate is the minimum voltage or minimum dv/dt; the second-best estimate is the second lowest local minimum; etc.)

The LAT estimates described above are sometimes referred to as "LAT annotation values."

The techniques disclosed herein assume that, devoid of noise and irregular galvanic connections, electrodes that are physically close to each other ("neighbor electrodes") and/or signals that are acquired at temporally neighboring heart beats exhibit similar annotation values. The signals extracted from neighbor electrodes and the LAT values that are annotated from such signals are referred to as "spatially related," whereas the signals extracted from temporally neighboring heart-beats and the LAT values that are annotated from such signals are referred to as "temporally related." Spatially and/or temporally related signals and annotation values will be referred to, collectively, as "related."

Embodiments according to the present invention take advantage of the expected similarity of related signals, to increase the reliability of the visualized LAT values.

In some embodiments, a processor annotates LAT values of a group of related intra-cardiac electrophysiological signals, e.g., using one of the four criteria that were mentioned above. The processor then calculates statistical characteristics of the group and determines, using a measure of deviation responsive to the statistical characteristics, which of the signals substantially deviates from the LAT values of the group (e.g., a signal for which the LAT value is not within a preset distance from the group average).

According to an embodiment, for signals that substantially deviate from the group values, the processor decides to reassess the LAT values, using the second-best estimate, the third best estimate, etc., until the processor finds a LAT value that does not substantially deviate from the group values. In an embodiment, the statistical characteristics comprise the mean of the LAT values (e.g., $\bar{x}=\Sigma x/n$) and the standard deviation (e.g., $\sigma=\sqrt{(\Sigma(x-\bar{x})^2/n)}$) of the group. The measure of the deviation is the Standard Score of the LAT value (defined as the difference between the value and the mean, divided by the standard deviation), which is compared to preset limits. For example, a substantially deviating LAT values may be defined as any value that is larger than the mean by more than 3.5 standard deviations (standard score=3.5), or lower than the mean by more than 1.5 standard deviations (standard score=1.5).

In summary, according to embodiments of the present invention, the quality and reliability of a group of annotation values of spatially related inter-cardiac signals that are visualized to a user may be improved in real time by calculating statistical characteristics of the annotation values, and recalculating LAT values that substantially deviate from the group values using next best estimates.

System Description

FIG. 1 is a schematic, pictorial illustration of an electro-anatomical system 21 for multi-channel measurement of intra-cardiac ECG signals, in accordance with an embodiment of the present invention. In some embodiments, system 21 is used for electro-anatomical mapping of a heart.

FIG. 1 depicts a physician 22 using an electro-anatomical catheter 23 to perform an electro-anatomical mapping of a heart 24 of a patient 25. Catheter 23 comprises, at its distal end, one or more arms 26, which may be mechanically flexible, to each of which are coupled one or more distal electrodes 27. As would be appreciated, although FIG. 1 depicts a catheter with five arms, other types of catheters may be used in alternative embodiments according to the present invention. The electrodes are coupled, through an interface 32, to a processor 34.

During the electro-anatomical mapping procedure, a tracking system is used to track the intra-cardiac locations of distal electrodes 27, so that each of the acquired electrophysiological signals may be associated with a known intra-cardiac location. An example of tracking system is Active Current Location (ACL), which is described in U.S. Pat. No. 8,456,182. In the ACL system, a processor estimates the respective locations of the distal electrodes based on impedances measured between each of distal electrodes 27 and a plurality of surface electrodes 28 that are coupled to the skin of patient 25 (For ease of illustration, only one surface-electrode is shown in FIG. 1). The processor may then associate any electrophysiological signal received from distal electrodes 27 with the location at which the signal was acquired.

In some embodiments, multiple distal electrodes 27 acquire intra-cardiac ECG signals from tissue of a cardiac chamber of heart 24. The processor comprises a signal acquisition circuitry 36 that is coupled to receive the intra-cardiac signals from interface 32, a memory 38 to store data and/or instructions, and a processing unit 42 (e.g., a CPU or other processor).

Signal acquisition circuitry 36 digitizes the intra-cardiac signals so as to produce multiple digital signals. The Acquisition Circuitry then conveys the digitized signals to processing unit 42, included in processor 28.

Among other tasks, processing unit 42 is configured to extract annotation parameters such as Local Activation Time ("LAT") from the signals, according to a selected criterion from a group of LAT estimation criteria, including (but not limited to) maximum ECG voltage, minimum ECG voltage, maximum positive rate-of-change of the ECG voltage and maximum negative rate-of-change of the ECG voltage. When the processing unit estimates a LAT according, for example, to the maximum ECG voltage criterion, the LAT value will equal the time when the Y-value of the ECG signal is at a maximum (for each cardiac cycle). Similarly, the estimated LAT may equal the time when the Y value is at a minimum, when the first derivative of the Y value is at its maximum, or when the first derivative is at its minimum.

Processing unit 42 is further configured to calculate statistical characteristics such as mean value of the annotated parameters for groups of neighboring signals that are likely to be similar (in the current context, neighboring signals refers to signals from electrodes located close to each other ("spatially related")).

According to embodiments, the acquired ECG signals may be noisy, due to poor galvanic connection, induced noise from various sources, noise in signal acquisition circuitry 36, or from any other source. In addition, pathological ECG signals such as those associated with atrial flutter and right bundle branch block may exhibit multiple voltage peaks and/or dips, as well as multiple dv/dt peaks and dips, per cardiac cycle. By comparing the LAT values of each of the signals of the group, the processing unit may determine that a LAT value which significantly deviates from the values of the group is likely to be erroneous. LAT values which are not likely to be erroneous (e.g., best estimate LAT value) are referred to hereinunder as valid LAT values.

In an embodiment, for any of the LAT estimation criteria, the processing unit may extract, in addition to the most likely value (which corresponds to the absolute maximum or minimum), a series of alternative LAT values, with descending likelihood. For example, for the maximum voltage criterion, the processing unit may be configured to find local maxima of the ECG signal, and then annotate the second best LAT estimate from the second highest maximum, the third best estimate from the third highest maximum, and so on. In a similar manner, the processing unit may construct a series of descending-likelihood alternative LAT values for any of the four criteria, by finding local maxima or minima of the voltage and the first derivative of the voltage of the ECG signal.

If processing unit 42 determines that a LAT value is not valid, the processing unit may try alternative LAT values, starting from the second best estimate, and proceeding to less likely LAT values, until a valid value (e.g. a LAT value that is not likely to be erroneous) is found (if the processing unit does not find any valid value, the processing unit may, for example, drop the signal, or use the probably erroneous best estimate).

In some embodiments, processing unit 42 uses the valid annotation values, for example, to construct an electro-anatomical map 50 of the heart and display it in real-time to physician 22 on a screen 52. Alternatively, processing unit 42 may present valid annotation values in any other suitable way.

The example illustration shown in FIG. 1 is chosen purely for the sake of conceptual clarity. In alternative embodiments of the present invention, for example, position measurements can also be done by applying a voltage gradient between pairs of surface electrodes 28 and measuring, with distal electrodes 27, the resulting potentials (e.g., using the CARTO®4 technology produced by Biosense-Webster, Irvine, Calif.). Thus, embodiments of the present invention apply to any position sensing method.

Other types of catheters, such as the Lasso® Catheter (produced by Biosense-Webster), or a basket catheter, may equivalently be employed. Contact sensors may be fitted at the distal end of electro-anatomical catheter 23. Other types of electrodes, such as those used for ablation, may be utilized in a similar way on distal electrodes 27 to acquire intra-cardiac electrophysiological signals.

FIG. 1 mainly shows parts that are relevant to embodiments of the present invention. Other system elements, such as external ECG recording electrodes and their connections are omitted. Various ECG recording system elements are omitted, as well as elements for filtering, digitizing, protecting circuitry, and others.

In an optional embodiment, a read-out application-specific integrated circuit (ASIC) is used for measuring the intra-cardiac ECG signals. The various elements for routing signal acquisition circuitry 36 may be implemented in hardware, e.g., using one or more discrete components, such as field-programmable gate arrays (FPGAs) or ASICs. In some embodiments, some elements of signal acquisition circuitry 36 and/or processing unit 42 may be implemented in software, or by using a combination of software and hardware elements.

Processing unit 42 typically comprises a general-purpose processor with software programmed to carry out the functions described herein. The software may be downloaded in electronic form, over a network, for example, or it may, alternatively or additionally, be provided and/or stored on non-transitory tangible media, such as magnetic, optical, or electronic memory.

Figure 2:
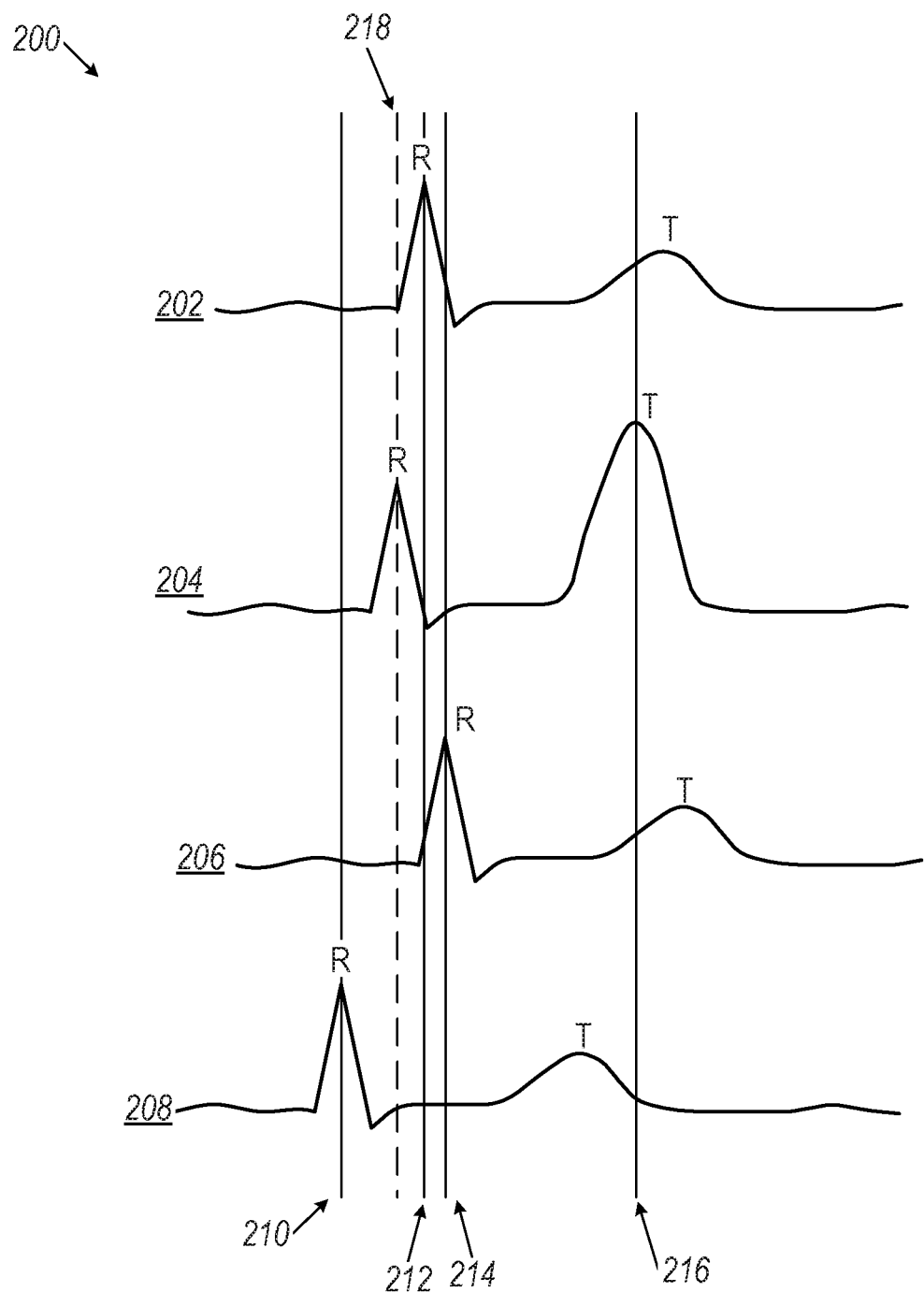
FIG. 2 is a diagram that schematically illustrates acquisition of signals by a group of spatially related electrodes, in a single cardiac cycle, in accordance with an embodiment of the present invention.

FIG. 2 is a diagram 200 that schematically illustrates acquisition of signals by a group of spatially related electrodes, in a single cardiac cycle, in accordance with embodiments of the present invention. The horizontal axis denotes time, and the vertical axis denotes voltage levels. Four signals are illustrated—a first-electrode signal 202, a second electrode signal 204, a third electrode signal 206 and a fourth electrode signal 208. Each signal exhibits an R peak followed by a T peak.

Processing unit 42 (FIG. 1) employs the maximum-voltage criterion to annotate the LAT values of the signals —A value 210, corresponding to the R peak of signal 208; a value 212, corresponding to the R peak of signal 202; and a value 214, corresponding the R peak of signal 206. Due to noise and/or pathology, for signal 204, the voltage of the T peak is higher than the voltage of the R peak, and hence, the initial LAT annotation (best LAT estimate) of signal 204 is a LAT value 216, corresponding to the peak of the T signal. However, the second-best estimate for signal 204 LAT (i.e., the second highest local maximum) is the R peak, which is represented by a LAT value 218.

According to the example embodiment illustrated in FIG. 2, LAT value 216 substantially deviates from the LAT values of the group. Processing unit 42 will, therefore, try an alternative value, starting with the second-best estimate. As LAT value 218 does not deviate from the LAT values of the group and therefore the most-likely annotation value, LAT value 218 is a valid LAT value.

Thus, using a relatively fast method that can be done in real-time, the processing unit can enhance the reliability of the annotated LAT value, by checking, in case the best LAT estimate significantly deviates from the LAT value of the group, LAT values associated with local maxima that are lower than the absolute maximum.

The example illustration shown in FIG. 2 is chosen purely for the sake of conceptual clarity. In alternative embodiments of the present invention, for example, more spatially related signals may be used; the number of local maxima may be more than two, and other LAT estimation criteria may be used.

Figure 3:
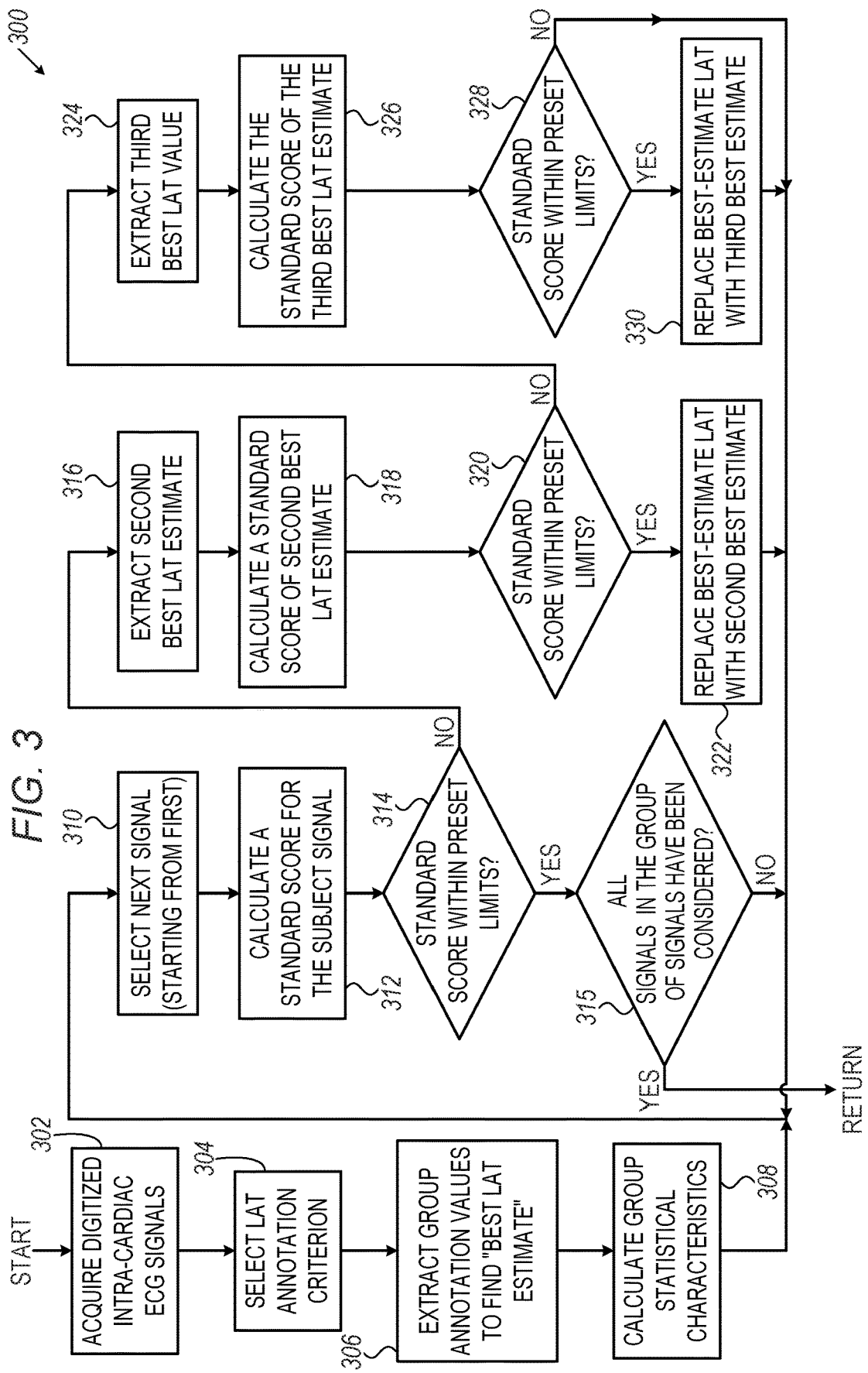
FIG. 3 is a flow chart that schematically illustrates a method for enhancing the reliability of annotation values, in accordance with an embodiment of the present invention.

FIG. 3 is a flow chart 300 that schematically illustrates a method for enhancing the reliability of annotation values, in accordance with an embodiment of the present invention. The method is executed by processing unit 42 (FIG. 1).

The method starts at an Acquiring Signals step 302, wherein the processing unit acquires a plurality of intra-cardiac ECG signals. The processing unit then, in a Selecting Group step 304, selects a group of related signals from the acquired signals. Such selection may be done, for example, using the CART®4 technology, or by other suitable techniques.

Then, in a Selecting Criterion step 304, the processing unit selects a LAT estimate criterion. The selected criterion may be, for example, one of maximum voltage, minimum voltage, maximum dv/dt and minimum (most negative) dv/dt. The selection may be instructed by a user or selected by any other means.

Using the criterion selected in step 304, the processing unit, at an Extracting Group Annotation Values step 306, extracts the LAT values of all group signals, by finding a best LAT estimate corresponding to the selected criterion. As an example, in FIG. 2, the processor may look at the group of signals (210-218) with LAT values 210, 212, 214, 216 and 218 and consider these values against a selected likelihood criterion to select LAT value 218 (e.g., from FIG. 2) as the "best LAT estimate" (or an LAT value which is not likely to be erroneous) in step 306 (in FIG. 3) to be a "valid annotation value" that may be graphically displayed.

It is noted that, depending on the results of statistical tests used in loops 310-314, 316-320 or 324-328, the processor may replace the best LAT estimate from step 306 with the best estimate of respective statistical test loops 316-320 (i.e., replace the first best estimate of step 306 with a second best estimate at step 322) or of loop 324-328 (to replace the first best estimate of step 306 with a third best estimate at step 330).

Next, in a Calculating Statistical Characteristics step 308, the processing unit calculates one or more parameters such as mean value, standard deviation, etc. of the group of LAT values.

After calculating the group statistics in step 308, the processing unit starts a loop (steps 310-314) in which the LAT annotation of each signal is checked against the statistical characteristics of the group (from step 308) and recalculated in case the LAT value significantly deviates from the group LAT values. That is, the processor checks for LAT value that is "statistically deviant" by more than a predefined measure of statistical deviation with respect to the group statistical characteristic obtained in step 308. The loop (steps 310-314) starts at a Selecting Next Signal step 310, wherein the processing unit selects a next signal from the list of group signals (e.g., signals 210-218 in FIG. 2) and, in a Calculating Standard Score step 312, calculates the standard score of the signal with respect to the group statistical characteristics (that is, the processors calculates the number of standard deviations between the LAT value of the signal and the group average).

The processing unit next, in a Comparing to Limits step 314, checks if the standard score of the LAT signal is within preset limits. If the LAT value is within the preset limits, such as, for example, 0.25, the processing unit will enter a Checking All Signals Considered step 315. If, in step 315, more signals are to be considered, the processing unit will reenter step 310, to check the next signal of the group; if, however, no more signals are to be considered, the flowchart will end (or, alternatively, may be rerun for another group of signals).

Steps 310-314 allow for the processor to identify any intra-cardiac signal in the group of intra-cardiac signals that have a "statistically deviant" annotation value; e.g.,—an annotation value that deviates from the group average by more than a predefined measure of statistical standard deviations.

If, at step 314, the LAT value of the signal is not within the preset limits, the processing unit enters an Extracting Second-Best LAT step 316 and calculates the second best LAT value (as described hereinabove in relation to step 312), calculates the standard score of the second best LAT in a Calculating Standard Score step 318, and, in a Comparing to Limits step 320, compares the standard score to preset limits.

If, in step 320, the standard score is within the preset limits, the second-best estimate is better than the first; the processing unit will enter a Replacing-Best by Second-Best step 322, and replace the best estimate LAT (from step 306) in the group of signals with the second best, and then reenter step 310 to check the next signal. If, however, in step 320, the standard score is not within the preset limits, the processing unit assumes that the second-best estimate is erroneous and tries the third-best estimate—in an Extracting Third-Best LAT step 324 the processing unit extracts the third best value; in a Calculating Standard Score step 326 the processing unit calculates the standard score of the third-best LAT estimate, and checks if the standard score is within preset limits in a Comparing to Limits step 328.

If, in step 328, the standard score is within the preset limits, the third-best estimate is better than the first best estimate in step 306 (and the second best estimate in step 316); the processing unit will enter a Replacing-Best by Third-Best step 330, replace the best estimate LAT (from step 306) in the group of signals with the third best and then reenter step 310 to check the next signal. If, however, in step 328, the standard score of the third-best estimate is not within limits, the best-estimate LAT should not be changed, and the processing unit reenters step 310 to check the next signal.

As described above, the flowchart ends at step 315, when there are no more signals of the current groups to be considered. The processing unit, at this stage, will have annotated LAT values for all the signals in the group. The processing unit may then re-enter the flowchart for another group of related signals, or perform other tasks that are beyond the scope of the present disclosure.

The example flow chart illustrated in FIG. 3 is chosen purely for the sake of conceptual clarity. In alternative embodiments, for example, the flow chart may comprise checking a fourth and/or further less-likely best estimates; in other embodiments, only the second-best estimate is checked. In some embodiments, less-likely estimates are calculated and stored as part of step 306 for the entire group, and hence steps 312, 318 and 326 are redundant. In some embodiments, some or all of the steps may be executed concurrently. Some typical alternative flow charts will be described with reference to FIG. 4.

Figure 4:
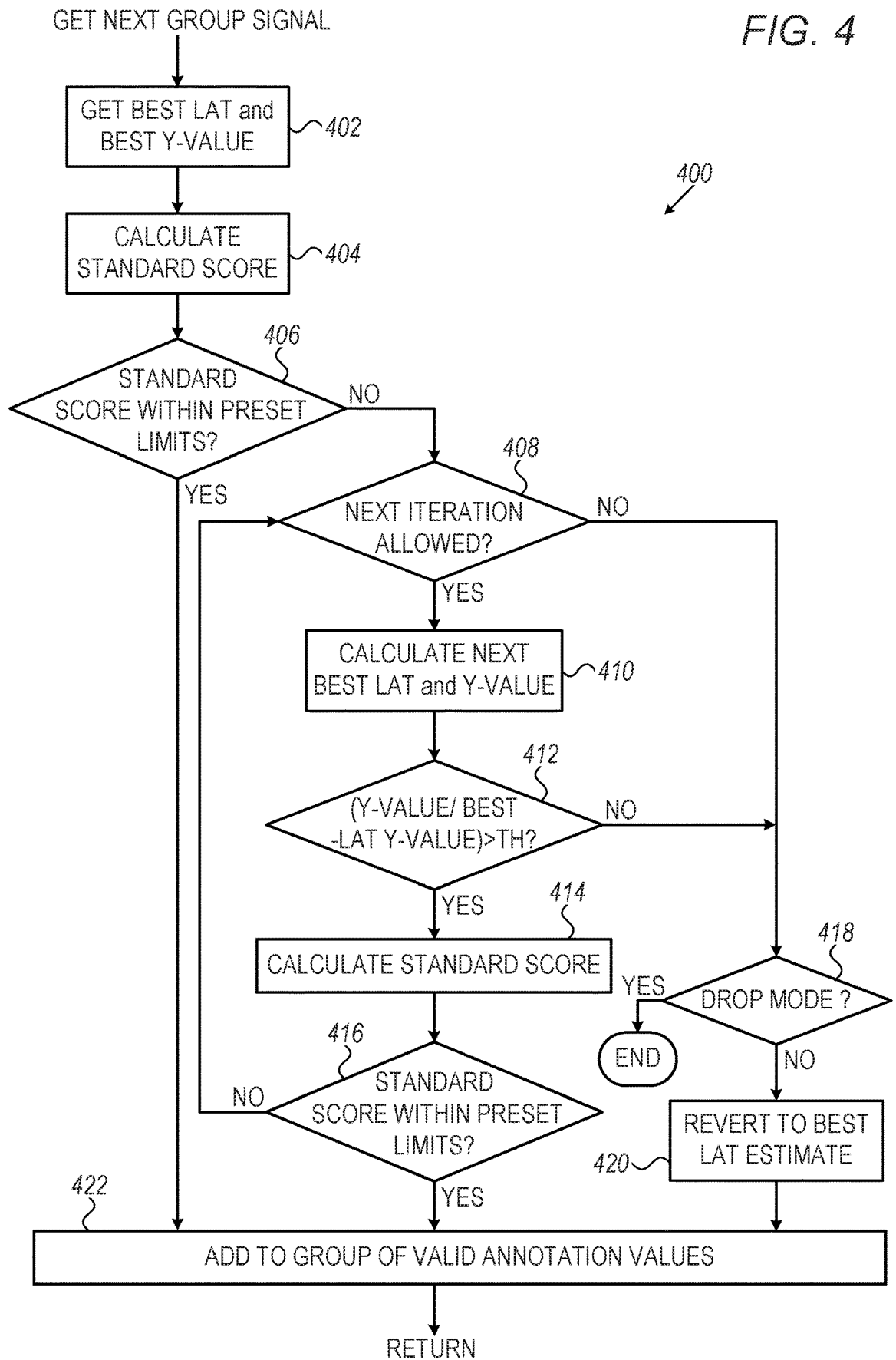
FIG. 4 is a flow chart that schematically illustrates a method for enhancing the reliability of annotation values of a group of spatially related LAT values, in accordance with an embodiment of the present invention.

FIG. 4 is a flow chart 400 that schematically illustrates a method for enhancing the reliability of annotation values of a group of spatially related LAT values, in accordance with an embodiment of the present invention. The method is executed by processing unit 42 (FIG. 1) after the statistical characteristics of the group is calculated, for each member of the group (e.g., after step 308, FIG. 3; note, though, that FIG. 4 replaces further steps of FIG. 3, from step 310 to step 330).

Unlike the example embodiment of FIG. 3, according to the method illustrated in FIG. 4, the processing unit, while examining the group of signals, creates a new group of valid LAT signals, which may then be visualized to the user.

The flow chart starts at a Getting Best LAT step 402, wherein the processing unit stores the best LAT and the corresponding Y value from the routine described in relation to the flow chart of FIG. 3. We may assume that the best LAT and the corresponding Y value were extracted when the processor calculated the group annotation values, e.g., in step 306, FIG. 3.

Next, in a Calculating Standard Score step 404, the processing unit calculates the number of standard deviations between the LAT value of the signal and the group average, and proceeds to a Comparing to Limits step 406, to check if the standard score of the LAT signal is within preset limits.

If the standard score of the LAT value is not within the preset limits, the processing unit will enter a Checking-if-Next-Iteration-Allowed step 408. When the processing unit first enters step 408, it will start a first iteration, and every time that the processing unit re-enters step 408, the iteration number will increase. In embodiments, there may be a limit to the number of iterations—for example, the processor may skip less likely estimates after the third best estimate (and hence, next-iteration will not be allowed in step 408 after three iterations). In another example, the processing unit may skip further iterations if there are no more local maxima or minima (according to the selected criterion).

If, in step 408, next iteration is allowed, the processing unit will enter a Calculating Next-Best LAT step 410, wherein the processing unit calculates the next best LAT and the corresponding Y value.

According to the example embodiment illustrated in FIG. 4, to qualify for a valid LAT value, a local maximum (or minimum, according to the selected criterion) should be substantial relative to the best estimate. For example, if the criterion is maximum dv/dt; the absolute maximum value is 25 mV/Sec and the second local maximum (second best estimate) is 1 mV/Sec, the processing unit may reject the second best estimate although the best estimate may deviate substantially from the group average.

The processing unit carries out this test in a Checking Y-Value ratio step 412, executed next to step 410. The processing unit divides the second-best estimate Y-Value (1 mV/Sec in the example above) by the Y value of the best estimate (25 mV/Sec) and compares the result (0.04) to a preset threshold. If the ratio is greater than the threshold, the processing unit proceeds to a Calculating Standard Score step 414 and calculates the standard score of the current LAT estimate relative to the group statistics, and the enters a Comparing to Limits step 416, to check if the standard score of the next-best LAT signal is within preset limits. If the standard score is not within the limit, the processing unit will re-enter step 408, and try the next best estimate.

According to the example embodiment illustrated in FIG. 4, the processing unit may be in a Drop-Mode, wherein invalid LAT values are not visualized (as opposed to visualizing the best estimate, although most probably erroneous). If, in step 408, no more iterations are allowed or if, in step 412, the ratio is too low, deeming the current best-LAT estimate invalid, there is no valid LAT value for the signal. The processing unit enters a Checking Drop Mode step 418; if Drop Mode is on, the process ends (and no valid value will enter the group of valid LAT values, and hence the LAT of the current signal will not be visualized). If, in step 418, Drop-Mode is off, the processing unit will enter a Reverting to Best Estimate step 420, and change the current LAT estimate to the best LAT which was stored in step 402.

If, in step 406, the best LAT is within the limits; or if, in step 416, a lower best estimate is within the limits; and, following step 420, the processing unit enters an Adding LAT to Valid LATs step 422, and adds the current LAT estimate to the group of valid LAT estimates, and the flow chart ends (or, typically, rerun for the next signal of the group).

As would be appreciated, the example flow chart illustrated in FIG. 4 is chosen purely for the sake of conceptual clarity. In alternative embodiments of the present invention, for example, there is no Drop Mode—in an embodiment invalid values are never visualized, and, in another embodiment, invalid values are always visualized. In yet another embodiment, the processing unit may decide whether to visualize or hide a non-valid LAT value according to a less constraining test; e.g.—a value will be visualized if its standard score deviates from the group mean by a threshold that is greater than the threshold used in steps 406 and 416. In some embodiments, invalid values are visualized but distinctly marked.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:
1. A system, comprising:
an intra-cardiac probe having multiple electrodes;

signal acquisition circuitry, which is configured to receive multiple intra-cardiac signals acquired by the multiple electrodes of the intra-cardiac probe in a heart of a patient; and a processing unit, which is configured to:
acquire a group of the intra-cardiac signals;
extract a respective most-likely annotation value from each of the intra-cardiac signals in the group, in accordance with a likelihood criterion;
identify in the group an intra-cardiac signal whose most-likely annotation value is statistically deviant in the group by more than a predefined measure of deviation;
extract, from the intra-cardiac signal having the statistically deviant most-likely annotation value, at least a second-most-likely annotation value in accordance with the likelihood criterion; and
responsive to a statistical deviation of the second-most-likely annotation value, select a valid annotation value for the corresponding intra-cardiac signal.

2. The system according to claim 1, wherein the processing unit is configured to define the measure of the deviation in terms of a standard score of the annotation values.

3. The system according to claim 1, wherein the processing unit is configured to calculate deviations of the annotation values over intra-cardiac signals acquired by a selected subset of spatially related electrodes located no more than a predefined distance from one another in the heart.

4. The system according to claim 1 wherein the processing unit is further configured to identify, for at least the statistically deviant most-likely annotation value, a group of alternative annotation values with decreasing likelihood ranks and to select the valid annotation value responsive to the statistical deviation and the likelihood ranks of the alternative annotation values.

5. The system according to claim 1, wherein the annotation values comprise Local Activation Times (LATs).

6. The system according to claim 1, wherein the processing unit is configured to extract the most-likely annotation value in a given intra-cardiac signal by finding an extremum of the given intra-cardiac signal in a cardiac cycle, and to extract the second-most-likely annotation value by finding a second-highest local extremum of the intra-cardiac signal.

7. The system according to claim 1, wherein the processing unit is configured to extract the most-likely annotation value in a given intra-cardiac signal by finding an extremum derivative of the given intra-cardiac signal in a cardiac cycle, and to extract the second-most-likely annotation value by finding a second-highest local extremum of the derivative.

8. A method, comprising:
receiving multiple intra-cardiac signals acquired by multiple electrodes of an intra-cardiac probe in a heart of a patient;
selecting a group of the intra-cardiac signals;
extracting a respective most-likely annotation value from each of the intra-cardiac signals in the group, in accordance with a likelihood criterion;
identifying in the group an intra-cardiac signal whose most-likely annotation value is statistically deviant in the group by more than a predefined measure of deviation;
extracting, from the intra-cardiac signal statistically deviant most-likely annotation least a second-most-likely annotation value in with the likelihood criterion; and
responsive to a statistical deviation of the second-most-likely annotation value, selecting a valid annotation value for the corresponding intra-cardiac signal.

9. The method according to claim 8, and comprising defining the measure of the deviation in terms of a standard score of the annotation values.

10. The method according to claim 8, wherein identifying the statistically deviant most-likely annotation value comprises calculating deviations of the annotation values over intra-cardiac signals acquired by a selected subset of spatially related electrodes located no more than a predefined distance from one another in the heart.

11. The method according to claim 8, wherein extracting at least the second-most-likely annotation value and selecting the valid annotation value comprise identifying, for at least the statistically deviant most-likely annotation value, a group of alternative annotation values with decreasing likelihood ranks and selecting the valid annotation value responsive to the statistical deviation and the likelihood ranks of the alternative annotation values.

12. The method according to claim 8, wherein the annotation values comprise Local Activation Times (LATs).

13. The method according to claim 8, wherein extracting the most-likely annotation value in a given intra-cardiac signal comprises finding an extremum of the given intracardiac signal in a cardiac cycle, and wherein extracting the second-most-likely annotation value comprises finding a second-highest local extremum of the intra-cardiac signal.

14. The method according to claim 8, wherein extracting the most-likely annotation value in a given intra-cardiac signal comprises finding an extremum derivative of the given intra-cardiac signal in a cardiac cycle, and wherein extracting the comprises finding a second-highest local extremum of the derivative.

15. A method to obtain a valid a local activation time of intra-cardiac electrocardiogram signals, the method comprising the steps of:
acquiring a group of digitized signals representing intra-cardiac electrocardiogram (ECG) signals;
extracting a first best estimate of a valid local activation time from the group of ECG signals;
calculating statistical characteristics for the group of ECG signals;
calculating a standard score for each signal in the group of ECG signals based on the group statistical characteristics;
comparing the standard score of each signal with preset limits; and
replacing the first best estimate of a valid local activation time with a local activation time of the signal having a standard score within the preset limits.

* * * * *